(12) United States Patent
Blanding et al.

(10) Patent No.: US 7,522,322 B2
(45) Date of Patent: Apr. 21, 2009

(54) APPARATUS FOR DENTAL SHADE MEASUREMENT

(75) Inventors: Douglass L. Blanding, Rochester, NY (US); Rongguang Liang, Penfield, NY (US); Edward J. Giorgianni, Rochester, NY (US); Steven J. Hansen, Pudong (CN)

(73) Assignee: Carestream Health, Inc., Rochester, NY (US)

( * ) Notice: Subject to any disclaimer, the term of this patent is extended or adjusted under 35 U.S.C. 154(b) by 1072 days.

(21) Appl. No.: 10/922,313

(22) Filed: Aug. 19, 2004

(65) Prior Publication Data

US 2006/0040230 A1 Feb. 23, 2006

(51) Int. Cl.
*H04N 1/46* (2006.01)
*H04N 1/04* (2006.01)
*G11B 11/00* (2006.01)
*G11B 13/00* (2006.01)

(52) U.S. Cl. ........................ 358/505; 358/509; 358/474; 358/475; 369/14; 369/16; 369/19; 369/21

(58) Field of Classification Search .................. 369/20, 369/29, 14, 16, 17, 18, 19, 21; 358/474, 358/475, 476, 482, 483, 493, 500, 509, 505; 378/168, 191
See application file for complete search history.

(56) References Cited

U.S. PATENT DOCUMENTS

| | | | |
|---|---|---|---|
| 5,107,285 A * | 4/1992 | Hamada et al. ............. 347/130 |
| 5,719,404 A * | 2/1998 | Tsai ....................... 250/559.29 |
| 5,759,030 A | 6/1998 | Jung et al. |
| 5,961,324 A | 10/1999 | Lehmann |
| 6,007,332 A | 12/1999 | O'Brien |
| 6,132,210 A | 10/2000 | Lehmann |
| 6,190,170 B1 | 2/2001 | Morris et al. |
| 6,206,691 B1 | 3/2001 | Lehmann et al. |
| 6,246,900 B1 * | 6/2001 | Cosman et al. ............. 600/426 |
| 6,305,933 B1 | 10/2001 | Lehmann |
| 6,328,567 B1 | 12/2001 | Morris et al. |
| 6,358,047 B2 | 3/2002 | Lehmann |
| 6,384,917 B1 | 5/2002 | Fradkin |
| 6,726,476 B2 * | 4/2004 | Jung et al. ..................... 433/26 |
| 6,813,010 B2 * | 11/2004 | Kono et al. .................... 356/71 |
| 7,010,162 B2 * | 3/2006 | Osawa et al. ................ 382/167 |
| 2002/0021439 A1 | 2/2002 | Priestley et al. |
| 2002/0032453 A1 * | 3/2002 | Cosman ....................... 606/130 |
| 2002/0063155 A1 * | 5/2002 | Tseng et al. ................. 235/454 |
| 2002/0064751 A1 * | 5/2002 | Lehmann ..................... 433/26 |
| 2002/0108623 A1 * | 8/2002 | Rehder et al. ............... 128/899 |
| 2003/0197806 A1 * | 10/2003 | Perry et al. .................. 348/370 |
| 2004/0152038 A1 * | 8/2004 | Kumagai et al. ............. 433/29 |
| 2004/0260367 A1 * | 12/2004 | De Taboada et al. .......... 607/88 |
| 2007/0036399 A1 * | 2/2007 | Matsumura et al. ......... 382/124 |

\* cited by examiner

*Primary Examiner*—Jerome Grant, II (57) ABSTRACT

An apparatus for suitable for obtaining an image of a dental structure has an illuminator member placed proximate the area to be imaged. The illuminator member has a support structure (30) for retaining the illuminator member in position proximate the area to be imaged. A reference (22) is coupled to the support structure (30) of the illuminator member and disposed within the area to be imaged. At least one light source (24) is coupled to the support structure (30) of the illuminator member for directing imaging illumination toward the area to be imaged. A camera (12) records an image from within the area to be imaged using the imaging illumination from the illuminator member, wherein the image comprises the reference (22).

45 Claims, 5 Drawing Sheets

APPARATUS FOR DENTAL SHADE MEASUREMENT

CROSS REFERENCE TO RELATED APPLICATIONS

Reference is made to commonly-assigned copending U.S. patent application Ser. No. 10/460,693, filed Jun. 12, 2003, entitled DENTAL COLOR IMAGING SYSTEM, Giorgianni et al., the disclosure of which is incorporated herein.

FIELD OF THE INVENTION

This invention generally relates to methods for obtaining an image under controlled illumination conditions and more particularly relates to an apparatus and method for obtaining colorimetric characterization of a tooth or other dental structure.

BACKGROUND OF THE INVENTION

Modern dental procedures often involve the fabrication of restorations such as crowns, implants, fixed partial dentures, and veneers. Ceramics are often used in such restorations because their optical properties are such that skillfully produced ceramic restorations can closely match the shape, texture, color and translucency of natural teeth.

Producing such realism involves a considerable degree of skill. Moreover, it requires that information regarding the color and other appearance characteristics of a patient's teeth be accurately determined and unambiguously conveyed to those who will be fabricating the restoration. While molds and other techniques can be used to record and transfer information regarding tooth shape and other geometric characteristics, techniques for determining and conveying color and other appearance characteristics are more problematic.

The most widely used techniques for determining and communicating tooth color information have changed little in the past seventy years. Typically, the process (referred to as "shade matching") involves visually matching a patient's tooth to one of a number of reference shade samples (shade tabs) within one or more sets of standardized shade guides. The person performing the match, often a dentist, records the identification of the matching shade tab and conveys that information to the dental laboratory where the restoration will be fabricated. The laboratory then uses its own set of the same shade guides to perform visual color evaluations of the restoration throughout the fabrication process.

The conventional visual shade matching process has a number of problems. The initial matching procedure is often long, difficult, and tedious. It is not unusual for the process to take twenty minutes or longer. In most cases, there will be no shade tab that perfectly matches the patient's teeth. Deciding which tab matches most closely (i.e., which mismatches the least) is often difficult. Frequently, the dentist may determine that the patient's teeth are particularly difficult to match. If this is the case, the patient may need to personally visit the orthodontics laboratory that will be fabricating the restoration. There, trained laboratory personnel can perform the color match. In many cases, the patient may then need to return to the dentist and laboratory two, three, or even more times as the color of the prosthetic is fine tuned by sequential additions of ceramics or other colored materials.

Despite the time and effort expended, this conventional visual color matching procedure fails (i.e., the prosthetic is rejected for color by the dentist and/or the patient) in about 10% of cases. Given the difficulty of the task, this rate of failure is not at all surprising. Visual color evaluation of relatively small color differences is always difficult, and the conditions under which dental color evaluations must be made are likely to give rise to a number of complicating psychophysical effects such as local chromatic adaptation, local brightness adaptation, and lateral-brightness adaptation. Moreover, shade tabs provide at best a metameric (i.e., non-spectral) match to real teeth; thus the matching is illuminant sensitive and subject to variability due to normal variations in human color vision (e.g., observer metamerism).

The difficulties associated with dental color matching have led to the development of a number of systems that attempt to replace visual assessments with instrumentation-based assessments using various types of spectrophotometric and calorimetric instruments. Although the idea of basing shade matching on objective measurements rather than on subjective visual color assessments seems appealing, such measurements are extremely difficult to perform in practice. As a result, reports from dentists and dental laboratory personal indicate that the level of performance of currently available instrument-based shade matching systems is not entirely acceptable. Uncertainties resulting from available instrument-based systems generally require that traditional visual assessments must still be performed for verification. Thus, much of the value of such systems is largely negated.

The failures and limitations of currently available shade-matching systems, both instrument-based and visual-based, can best be understood by examining the difficulties involved in matching the appearance of human teeth. First, tooth color is a complex interaction of reflection, transmission, refraction, fluorescence, and scattering by a variety of organic and inorganic components. It is influenced by variations in tooth pulp volume, dentin condition, enamel composition, and other variations in the composition, structure, and thickness of the dental tissues. One result of this complexity is that color appearance and color measurement are greatly influenced by lighting geometry, surrounding colors, and other environmental factors.

A further complication is that color is generally not uniform within a single tooth. Color non-uniformities may result from spatial variations in composition, structure, thickness, internal and external stains, surface texture, fissures, cracks, and degree of wetness. As a result, measurements based on relatively large areas produce averaged values that may not be representative of a tooth's dominant color. In addition, natural color variations and non-uniformities make it unlikely that a given tooth can be matched exactly by any single shade tab. This means that a method for conveying the distribution of color within a tooth, not just its average color, is required. Tooth color also is seldom uniform from tooth to tooth. Therefore, the ideal color of a restoration may not be an exact match to that of an adjacent tooth or to any other single tooth in a patient's mouth. Dentists use the word "harmony" to describe how a restoration should appear to blend with the various colors of a patient's teeth. The ideal color of a restoration may, for example, be somewhere between that of several nearby teeth, or it may be closer to the color of a similar tooth elsewhere in the mouth.

A further difficulty is that successful color communication requires that tooth color can be measured and specified according to a set of absolute reference color standards, such as numeric colorimetric values or reference shade tab identifiers. It is particularly important that the luminance factor is determined and conveyed accurately; yet luminance factor generally is the most difficult aspect of color to measure. Furthermore, error tolerances for all aspects of tooth color are extremely small. In the mouth, a reconstruction such as a single crown is immediately adjacent to natural teeth. This proximity makes even small color errors very apparent. Moreover, people generally are particular about the appearance of their teeth. Understandably, they are quite intolerant of restorations that appear inappropriate in color.

Lighting is an additional source of difficulty in performing dental color measurements. The type of lighting, the lighting geometry, and other factors must be appropriate for measurement purposes. In particular, specular reflections from the tooth surface must be avoided. At the same time, however, the measurement conditions must be consistent with those under which the results ultimately will be judged. These two needs are often in conflict; optimum conditions for making dental measurements generally are quite different from those of the real world.

Additionally, visual color assessments and objective measurements must be made in inherently difficult environment, i.e., the mouth of a live patient. Factors such as hygiene, aesthetics, and patient comfort are important and must be considered in the design of the assessment or measurement techniques. Speed is also a concern. If the patient's mouth is open, the teeth begin to dry in a relatively short period of time. This drying changes the relative refractive index of the surface, which lightens and desaturates the apparent color of the teeth. Instrument measurements or visual matches made under such conditions will likely lead to poorly matched prosthetics.

Color assessments, specifications and communication are further complicated by a lack of accurate color calibration within the dental industry. For example, studies have shown that there can be considerable variation even among supposedly identical sets of shade tabs from the same manufacturer. These variations make color communication based on such tabs ambiguous. For example the matching shade tab selected by a dentist may differ from the actual tab that will be used for reference at the laboratory fabricating the prosthetic, even though both tabs have the same identification and are assumed to be identical. As a result, a prosthetic built to match the color of the laboratory's shade tab will not match the color intended by the dentist. It would be valuable, then, for both the dentist and the dental laboratory to have a reliable and unambiguous means for specifying color. In addition, it would be valuable for the dentist and/or dental laboratory to have a means for verifying that a restoration meets a prescribed shade specification. At a dental laboratory, it would also be valuable to have a verification process incorporated in the fabrication process to provide shade guidance at intermediary stages of that process. Color adjustments then could be incorporated in subsequent fabrication stages.

Although a number of shade-matching systems have been described in the prior art, none fully addresses all the issues addressed above. For example, in a series of patents, including U.S. Pat. Nos. 6,358,047; 6,305,933; 6,206,691; 6,132,210; and 5,961,324 (all to Lehmann et al.), disclose a tooth shade analyzer system in which the preferred embodiment is based on the use of an intra-oral camera providing red, green, and blue (RGB) color values that are subsequently normalized and then used to derive hue, saturation, and intensity (HSI) values using a single set of RGB-to-HSI conversion equations. The derived HSI values are then compared to those derived from corresponding RGB measurements taken of a collection of shade tabs. Similarly, in U.S. Pat. Nos. 6,190,170 and 6,328,567 (both to Morris et al.) a system that uses two or more references to normalize RGB image values from one or more digital cameras is disclosed. Again, teeth and shade tabs are compared according to their RGB values or to HSI or other values derived from RGB values using a single set of conversion equations. Similarly, U.S. Pat. No. 6,384,917 (Fradkin) discloses a system that uses beam splitters and other optical components to obtain RGB image values. Once again, teeth and shade tabs are compared according to their RGB values or to HSI or other values derived from RGB values using a single set of conversion equations. U.S. Patent Application Publication No. 2002/0021439 A1 (Priestley et al.) also discloses a color matching system in which colors are analyzed in terms of RGB values. The underlying assumption in all these descriptions is that the color of a tooth (i.e., its visual color appearance) can be matched by a shade tab having the same RGB values (or HSI or other values derived from those RGB values using a single set of conversion equations). However, that assumption is not generally true. The spectral reflectances of shade tabs differ from those of natural teeth; thus, visual matches between teeth and tabs are metameric, rather than spectral, matches. Furthermore, the spectral sensitivities of current digital cameras, including conventional and intra-oral cameras, are not equivalent to a set of visual color matching functions. As a result, matches determined from RGB measurements, or from HSI or other values derived by applying any given single set of conversion equations to measured RGB values, generally do not result in accurate visual matches. It is quite possible, for example, that a tooth and a shade tab may have identical RGB values, and thus identical derived HSI values; but still not match visually. It is also quite possible that a tooth and a shade tab may have different RGB values, and thus different derived HSI values; yet match visually. Such occurrences are a consequence of the basic nature of metameric matching.

U.S. Pat. No. 6,007,332 (O'Brien) discloses a tooth color matching system based on producing a photograph image of a tooth together with a visually selected color standard, such as a dental shade tab, and analyzing the photographic image using a calorimetric or spectrophotometric device. Using colorimetric or spectrophotometric devices in this manner does not address the fundamental problems associated with the metamerism of natural teeth and shade tabs because the devices are used to analyze the color of the resulting photograph, not the color of the original tooth and shade tab. The color comparison therefore will be subject to metamerism problems resulting from the fact that, like digital cameras, photographic media have RGB spectral sensitivities that are not equivalent to a set of visual color matching functions. Thus, a tooth and shade tab that match perfectly in the photographic image (visually, calorimetrically, and spectrally) still may not match visually in real life.

Other shade-measuring systems attempt to avoid problems related to metameric matching by using spectrophotometers or calorimeters for direct shade measuring. However, the geometry and other characteristics of the lighting used on such systems described in the prior art generally do not correspond to the lighting conditions under which teeth normally would be viewed. Spectrophotometric or calorimetric measurements made under non-representative lighting conditions may produce non-representative color values that result in unsatisfactory visual matches under normal viewing conditions. Moreover such systems do not provide images of the full mouth, or even of adjacent teeth. Thus, they do not provide information required to ensure a shade match that is harmonious in color with the surrounding teeth and mouth structure, nor do they convey other important information related to tooth appearance such as texture and gloss.

Some camera-based solutions described in patent literature also rely on lighting that is not representative of the lighting conditions under which teeth normally are viewed. For example, U.S. Patent Application Publication No. 2002/

0021439 (Priestley et al.) discloses a system in which cross-polarization is used to reduce glare from the tooth front surface. However, shade matches achieved under such lighting conditions may not necessarily match under more normal ambient light conditions. U.S. Pat. No. 5,759,030 (Jung et al.) discloses a method for determining optical characteristics of teeth in which light is provided by a central source fiber optic and detected by an array of perimeter receiver optics. Again, shade matches and other tooth characteristics measured under such lighting conditions may not necessarily correspond to those observed under normal conditions.

Commonly-assigned copending U.S. patent application Ser. No. 10/460,693 (Giorgianni et al.) addresses methods and requirements for obtaining an accurate colorimetric profile from data measured from the tooth. The matching of natural teeth with shade tabs and prosthetics is fundamentally metameric, not spectral. In addition, natural teeth and some ceramic materials exhibit fluorescence and other behaviors influenced by lighting characteristics. Therefore, the spectral energy distribution properties of the light source used for shade matching must be representative of sources under which the quality of the prosthetic ultimately will be judged. For measurement purposes, the lighting must provide an area of illumination that is substantially uniform in the plane of the target tooth and of an intra-oral reference. The illumination must also be sufficiently uniform in depth so that the front-to-back positioning of the target tooth is not overly critical. For measurement purposes, the lighting must minimize or eliminate specular reflections from the measurement areas of the target tooth and intra-oral reference. For measurement purposes, the lighting apparatus must provide repeatable illumination angle, intensity, and chromaticity from one exposure to the next. (However, the use of an appropriate photographic reference and the exposure-compensation methods of this invention can somewhat reduce the requirements for such repeatability.) The light available prior to exposure must be sufficient to allow proper positioning of the patient and focusing of the camera. Ideally, there should be a provision for previewing the lighting prior to camera exposure.

Patient comfort is a key consideration for illumination components. The lighting system should not cause the patient discomfort, such as by producing an undue amount of heat. The lighting pattern should be restricted so that little or no direct light reaches the patient's eyes. Bulky and cumbersome apparatus requiring continual checks or adjustments would not be favorable; ideally, illumination should require little or no adjustment. Test references that provide benchmark calibration should be manageable in size and, ideally, should not require the assistance of a technician or patient to hold the reference in place while a measurement is obtained.

As described in the commonly-assigned U.S. patent application Ser. No. 10/460,693 by Giorgianni et al. application cited above, an illumination angle of substantially 30 degrees has been found to be most favorable for shade matching. Uniform illumination provided at this optimal angle helps to minimize specular reflection that can have an adverse affect on color shading data. It has also been observed that the use of a fixed angle of illumination is important; otherwise, even slight angular changes in incident light can affect the colorimetric profile obtained.

In addition to requirements for suitable, fixed illumination angle, for positioning of a reference target, and for overall patient comfort, there are other practical considerations, including cost, size, flexibility, adaptability for use without requiring training, and ease of use in the dental examination environment. Thus, it can be seen that there is a need for an apparatus that enables color measurements for color shade matching and meets demanding requirements for accuracy, suitability, and ease of use.

In a broader context, there are other applications for which control of various illumination characteristics such as incident angle, color temperature, and brightness can significantly impact the usefulness of the images obtained. Applications of special interest can be found in dental and medical imaging, machine vision applications, and surface inspection applications, for example. Thus, in addition to meeting specific needs for improvement of dental color measurement as outlined above, there would also be benefits to imaging illumination solutions that serve a wide range of uses.

SUMMARY OF THE INVENTION

It is an object of the present invention to provide an apparatus for obtaining dental imaging data that meets the requirements stated in the background section above. With this object in mind, the present invention provides an apparatus for obtaining an image comprising:
 (a) an illuminator member placed proximate the area to be imaged and comprising:
  (i) a support structure for retaining the illuminator member in position proximate the area to be imaged;
  (ii) a reference, coupled to the support structure of the illuminator member and disposed within the area to be imaged;
  (iii) at least one light source coupled to the support structure of the illuminator member for directing imaging illumination toward the area to be imaged; and
 (b) a camera for recording an image from within the area to be imaged using the imaging illumination from the illuminator member, wherein the image comprises the reference.

From the aspect of obtaining an image for dental shade measurement, the present invention provides an imaging apparatus for obtaining a dental image from a patient comprising:
 (a) an intra-oral retainer held in the patient's mouth for illuminating an area of interest, comprising:
  (i) a reference coupled to the retainer, disposed within the area of interest;
  (ii) at least one light source coupled to the retainer for directing illumination toward the area of interest; and
 (b) a camera for recording an image from the area of interest using illumination from the light source.

It is a feature of the present invention that it applies controlled illumination to a tooth or other localized structure at a predetermined incident angle for providing consistent imaging conditions.

It is an advantage of the present invention that it provides a method for obtaining an image of teeth with minimized spectral highlights.

It is a further advantage of the present invention that it provides consistent illumination, from one image to the next.

It is a further advantage of the present invention that it provides a mechanism for placing a reference near the teeth or other structure being imaged, without requiring hand-held support.

It is yet a further advantage of the present invention that it allows ease of use of a camera in the dental office environment, eliminating the need for extensive training in techniques for assessing color match.

It is yet a further advantage of the present invention that it allows a degree of independence between the camera and the subject to be imaged, allowing a flexible arrangement of components that are relatively easy to use by untrained personnel.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

DETAILED DESCRIPTION OF THE INVENTION

The present description is directed in particular to elements forming part of, or cooperating more directly with, apparatus in accordance with the invention. It is to be understood that elements not specifically shown or described may take various forms well known to those skilled in the art.

The apparatus and methods of the present invention are ideally suited to an apparatus for obtaining images of teeth for dental color measurement. However, it must be observed that other adaptations of the apparatus and method of the present invention may be used for imaging other structures, including living tissue or inanimate objects.

Figure 1:
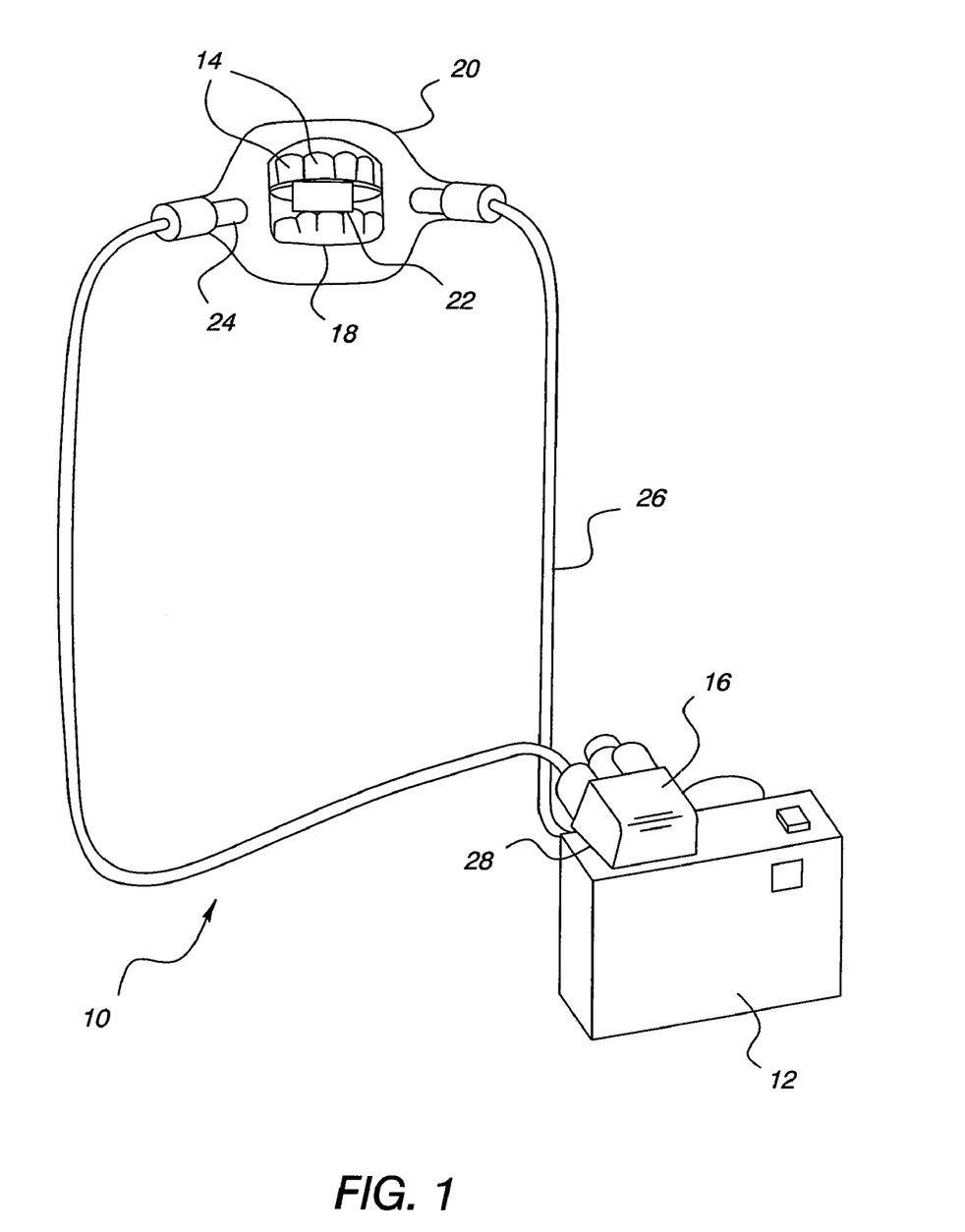
FIG. 1 is a perspective view showing components of an imaging apparatus according to the present invention.

Referring to FIG. 1, there is shown a dental imaging apparatus 10 according to one embodiment. A camera 12, such as a digital camera, is used to obtain one or more images of teeth 14 for a dental patient. A retractor 20, a type of retainer held in the patient's mouth, defines an imageable area 18. Retractor 20 supports a target reference 22, which provides a suitable material composition and color for providing a benchmark to the image obtained. One or more light sources 24 are mounted onto retractor 20, at a suitable angle for providing incident illumination to teeth 14. In the embodiment of FIG. 1, light sources 24 route light from a flash unit 16 to retractor 20 using one or more optical fibers 26. A hood 28, fitted onto camera 12, couples light from flash unit 16 to optical fibers 26. With this arrangement, flash timing of camera 12 is adapted for illumination of imageable area 18. This arrangement is advantaged in using the flash illumination source that has been designed for the camera, so that color temperature or other spectral considerations as well as flash timing need not be changed.

Figure 2:
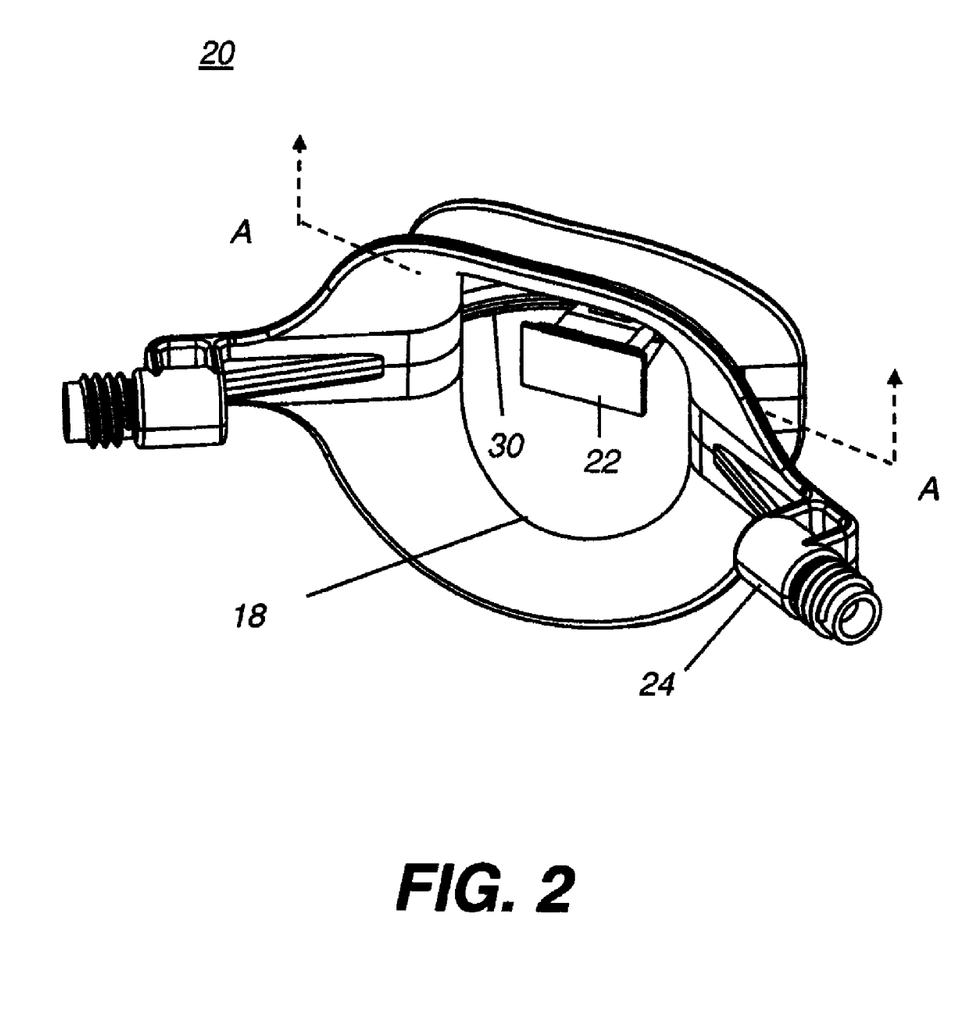
FIG. 2 is a perspective view showing a retainer that defines the imageable area and positions the reference.
Figure 3:
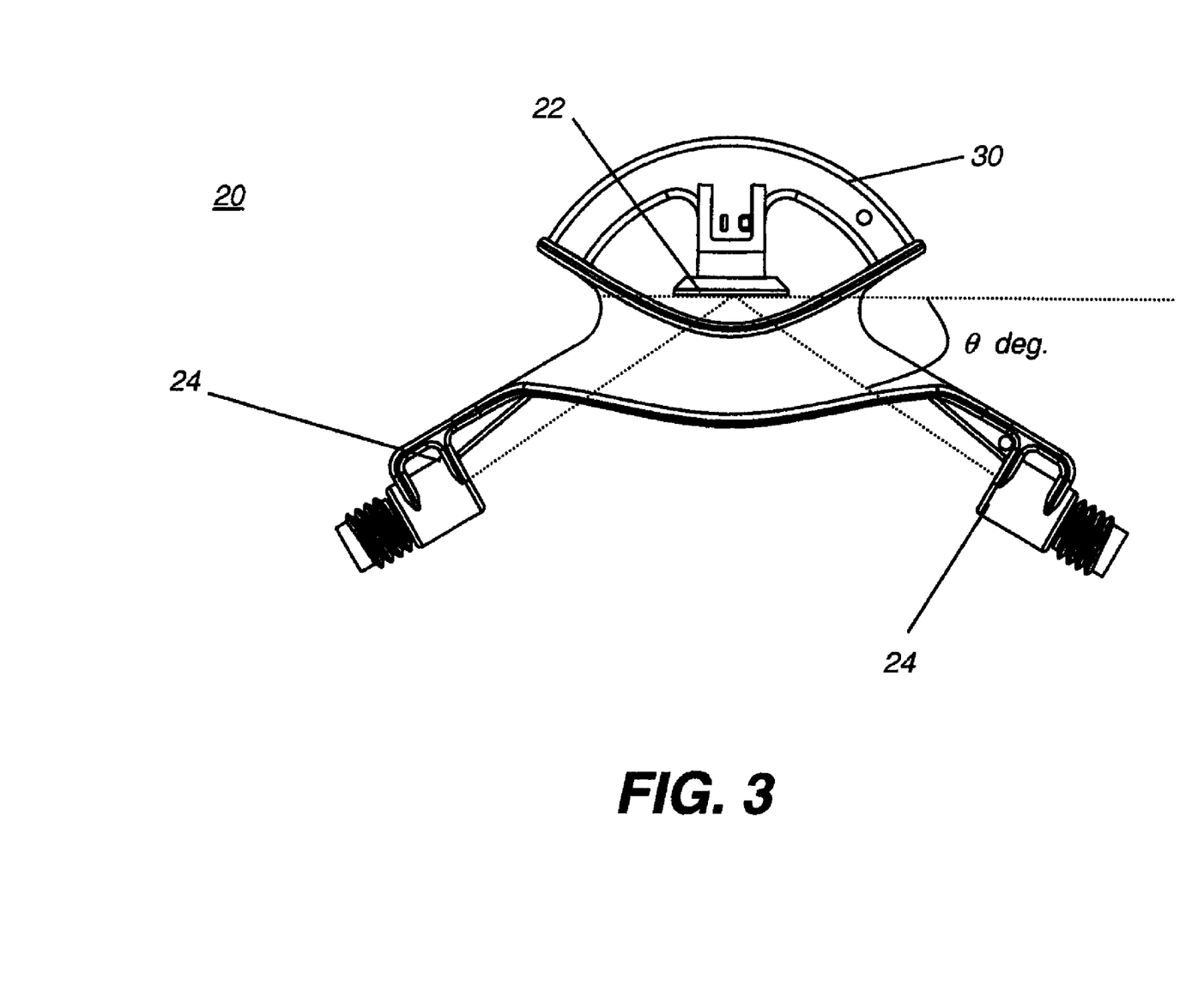
FIG. 3 is a top view of the retainer.
Figure 4:
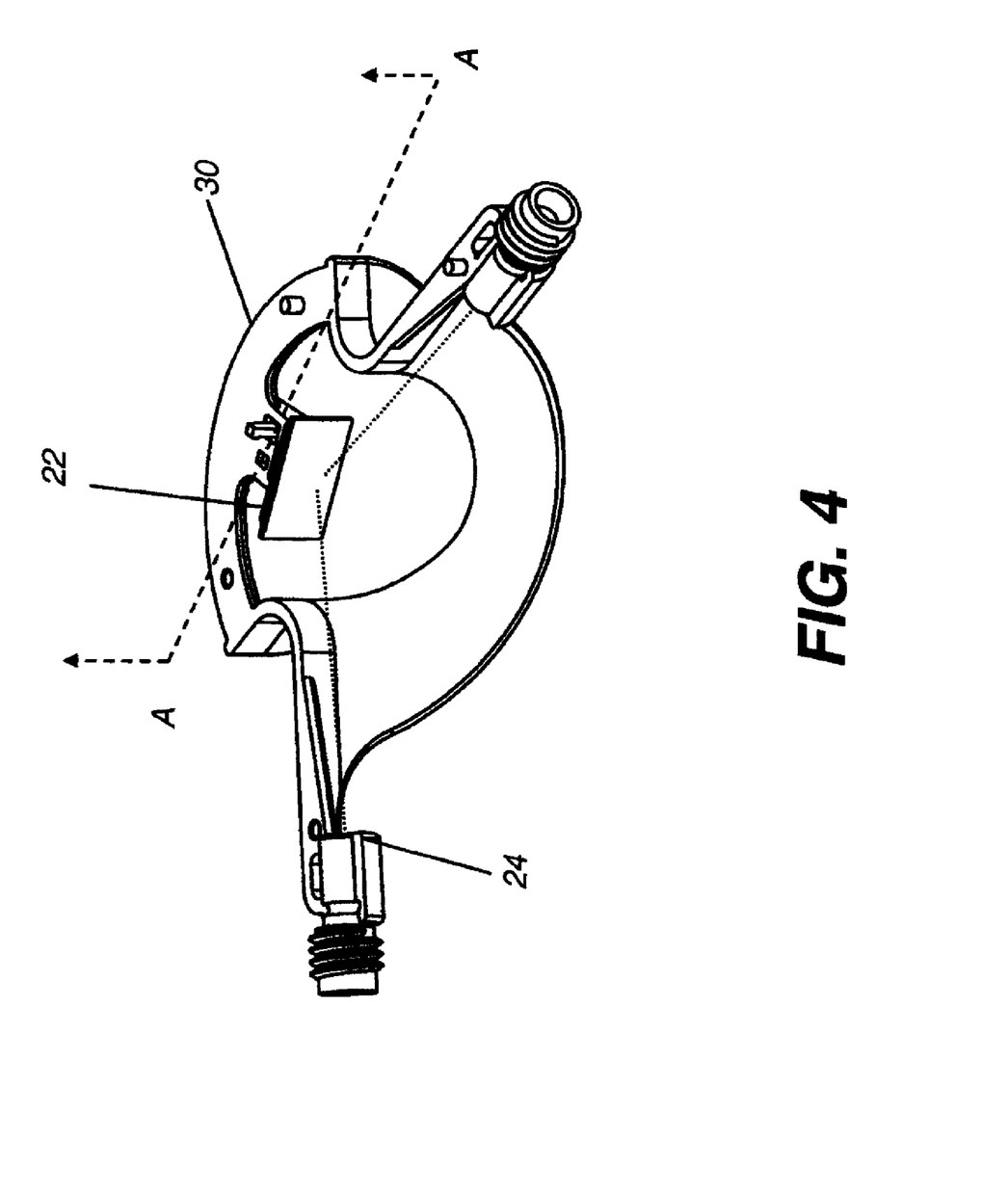
FIG. 4 is a cutaway top view of the retainer, showing its construction.

Referring to FIG. 2, there is shown a perspective view of retractor 20 that acts as an illuminator member in one embodiment. Here, retractor 20 frames imageable area 18. Within imageable area 18 is a support member 30 that supports target reference 22 in position. FIG. 3 shows a top view of retractor 20, showing key angular relationships used in one embodiment. FIG. 4 shows a cross-sectional perspective view from above, taken from the plane of line A-A in FIG. 2. As was noted in the commonly-assigned copending U.S. patent application Ser. No. 10/460,693 by Giorgianni et al. cited above, the incident angle of illumination, shown as angle θ in FIG. 3, can be particularly significant for dental color shade measurement applications. With one system, a fixed angle of substantially 30 degrees has been found to be particularly well-suited to the illumination requirements for dental color shade measurement. In the embodiment shown in FIGS. 1-4, this fixed illumination angle is built into the structure of retractor 20 itself. With the embodiment of FIG. 1, the action of mounting optical fibers 26 to retractor 20 automatically sets the illumination angle of light sources 24 at the optimal predetermined inclination.

Alternative Embodiments for Dental Imaging

The component arrangement shown in FIGS. 1-4 admits any of a number of alternative embodiments. For example, light source 24 can be embodied using separate lamps, LEDs, or other emissive sources mounted onto or apart from retractor 20, with illumination controlled from camera 12 or by some other means. It may be advantageous to connect optical fibers 26 to an alternate flash apparatus that is in communication with camera 12. Light sources 24 can be optically coupled to the flash lighting provided by camera 12, such that light sources 24 illuminate when stimulated by light from camera 12 in "slave flash" manner. A single light source 24 may be provided; alternately two or more light sources 24 could be provided, with any suitable arrangement for directing incident light at a predetermined angle. Flash operation may not be required; for some applications, steady-state illumination may be preferred. Separate light sources 24 may be provided for previewing and for image capture. Multiple emissive sources can be optically combined onto the same optical path, to provide light of different wavelengths, for example, including non-visible wavelengths, using techniques well known to those skilled in the optical design arts. Optionally, light sources 24 may be physically coupled to retractor 20 at different incident angles, with different arrangements of light sources 24 selected for particular imaging applications. Any number of lenses or other optical components, including polarizers or filters, could be employed for conditioning the output light from light source 24. In general, a key benefit of retractor 20 design relates to providing illumination of the correct type at an optimal incident angle, without necessitating adjustment or alignment by an operator or requiring manual manipulation by the dentist, a technician, or a patient. In the embodiments described herein, light sources 24 are coupled to retractor 20 at a fixed angle, determined to be the optimal angle for color shade measurement using a particular camera. Certainly, in an alternate embodiment, light source 24 could be mechanically coupled to retractor 20 in such a way that allows some amount of adjustment.

It must be noted that the illumination beam(s) may not be directed so that they intersect on the surface of reference 22, as is shown in the example of FIG. 3. The direction of the illumination beam is, typically, in the general direction of reference 22; however, the requirements of the individual reference 22 material and overall application dictate the actual geometry and preferred angles of incidence used.

Retractor 20 as shown in FIGS. 1-4 is just one example of a number of alternative types of support structures to which light source 24 and reference 22 can be coupled for providing an illuminator member. For dental applications, the design of retractor 20 has obvious advantages for use by a dentist or dental technician, providing retraction of the lips as well as supporting both light source(s) 24 and reference 22 in position. Retractor 20 can be molded or otherwise fabricated from any of a number of materials, including stainless steel or other metals, and plastics, for example. For some applications, it may be preferable to use a disposable retractor 20 fabricated from nylon or plastics; other applications may benefit from a sterilizable stainless steel structure.

Figure 5:
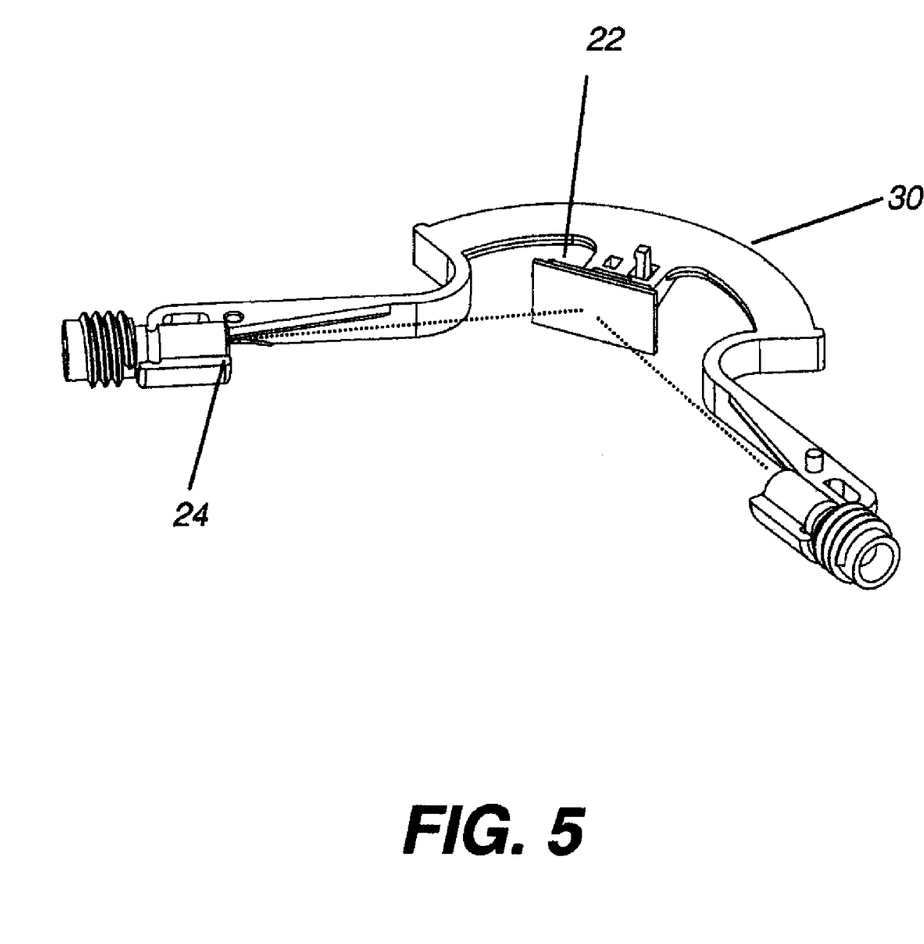
FIG. 5 is a perspective view showing a minimal support structure for providing illumination and reference in an alternate embodiment.

In some cases, however, a dentist may prefer to use different retraction mechanisms. For such cases, a simpler configuration may be more suitable. Referring to the embodiment of FIG. 5, support member 30 supports both light source(s) 24 and reference 22 in the needed relationship. The patient need only bite down on support member 30; other retractors would then typically be provided by dental personnel, as needed.

For dental color measurement, reference 22 is preferably fabricated from a ceramic or plastic, or suitably coated material selected for its compatible response to incident light. In one embodiment, a ceramic material is advantageously used, due to its similarity in response to that of natural tooth material. Depending on system complexity, reference 22 may be interchangeable, allowing an approximate initial measurement using one of a set of standard shades, for example. Or, reference 22 may be a standard target used to calibrate camera 12, such as a neutral target. Reference 22 may be monochrome or may contain multiple colors. To facilitate identification, reference 22 may be labeled with an identifying number or other markings. In other embodiments, reference 22 may provide a scale showing units of linear or angular measurement or may provide reference information on environmental conditions, such as temperature, pressure, relative humidity, or acidity, for example.

In one embodiment, camera 12 is a digital camera, such as the KODAK EASYSHARE DX 6490 Digital Camera, equipped with a close-up adapter lens. However, camera 12 could also be a conventional device for recording onto photosensitized film. In a dedicated application, a simpler CCD sensor, or other photosensor, could be deployed as a single-function camera for color measurement or other imaging using this system. Optionally, a color measurement instrument such as a calorimeter or spectrophotometer could be used in the place of camera 12 for obtaining colorimetric data directly.

Operation for Dental Shade Measurement

The operation of dental imaging apparatus 10 of FIG. 1 is straightforward and is compatible with the data-gathering required for use in the method disclosed in the commonly-assigned U.S. patent application Ser. No. 10/460,693 by Giorgianni et al. application cited above. For one embodiment, reference 22 is selected and is positioned in retractor 20. Optical fibers 26 are connected to retractor 20, which is then placed in a suitable position in the patient's mouth, near the tooth or other structure to be measured. The patient can then relax and wait for imaging to be completed. Hood 28 is connected to optical fibers 26 and is fitted onto flash unit 16 of camera 12. The dentist or dental technician then adjusts focus and operates camera 12 to obtain suitable images for color measurement. In practice, it has been shown that the arrangement of retractor 20 allows a reasonable amount of flexibility for the operator of camera 12. Camera 12 can be operated by hand in the normal manner, not requiring a stabilizing stand or mount for camera 12 support during image capture.

The images obtained are then transmitted to a dental lab or other facility at which the needed dental structure is to be fabricated. Transmittal of the image may take any of a number of possible forms. For example, digital camera 12 may be connected directly to a networked computer for data transfer directly to the lab. For a film-based camera, the exposed film or a print can be forwarded to the dental lab. Image data could also be recorded onto a removable medium, such as a diskette or CD, and shipped by mail or by courier, along with an accompanying mold, X-ray image, or other material.

Alternate Embodiments for Other Types of Imaging

While the apparatus and method of the present invention are ideally suited to the requirements of dental shade measurement, there are other additional applications that would benefit from an illumination member such as retractor 20, outfitted with a suitable imaging light source 24 and defining an imageable area 18 within which a reference 22 is disposed. The apparatus and methods of the present invention are particularly useful for applications in which color information must be accurately obtained and communicated and for which the angle, type, spectral characteristics, and brightness of illumination must be carefully controlled. Such applications can include, for example, any of a number of health imaging applications in which remote diagnosis is performed using patient images of a localized area or test results for assessment of a surface or object where color information is particularly important. Retractor 20 or a similar retainer used as the illuminator member can be freestanding, held in place by a patient or held in place by an externally provided device, or maintained in place using any of a number of possible mechanisms, including magnetism, suction, elastic bands, VELCRO hook-and-loop fastener (VELCRO is a trademark of Velcro, USA, Manchester, N.H.), a mechanical fitting, or a suitable adhesive, for example.

It can be seen that the apparatus and method of the present invention provide the advantages of ease of use and consistent, optimal lighting for dental color shade measurement applications. The overall structure of dental imaging apparatus 10 is relatively simple, yet allows a number of modifications to suit different requirements, including requirements of dental and other medical applications as well as a number of machine vision applications.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention.

Thus, what is provided is an apparatus and method for obtaining colorimetric characterization of a tooth or other structure.

PARTS LIST 10 dental imaging apparatus
12 camera
14 teeth
16 flash unit
18 imageable area
20 retractor
22 reference
24 light source
26 optical fiber
28 hood
30 support member

The invention claimed is:

1. An apparatus for obtaining an image comprising:
(a) an illuminator member placed proximate an area to be imaged and comprising:

(i) a support structure for retaining the illuminator member in position proximate the area to be imaged;

(ii) a reference, coupled to the support structure of the illuminator member and disposed within the area to be imaged, wherein the reference is removable;

(iii) at least one light source coupled to the support structure of the illuminator member for directing imaging illumination toward the area to be imaged; and (b) a camera for recording the image from within the area to be imaged using the imaging illumination from the illuminator member, wherein the image comprises the reference.

2. An apparatus according to claim 1, wherein the reference is a color reference.

3. An apparatus according to claim 1, wherein the reference displays measurement units.

4. An apparatus according to claim 1, wherein the at least one light source is an LED.

5. An apparatus according to claim 1, wherein the at least one light source is optically coupled with a flash apparatus of the camera.

6. An apparatus according to claimed 1, wherein the at least one light source is electrically coupled with a flash control signal of the camera.

7. An apparatus according to claim 1, wherein the at least one light source comprises an optical fiber.

8. An apparatus according to claim 1, wherein the camera is a digital camera.

9. An apparatus according to claim 1 wherein the support structure is held in position by magnetic attraction.

10. An apparatus according to claim 1, wherein the support structure is held in position by suction.

11. An apparatus according to claim 1, wherein the support structure is held in position in the mouth of a patient.

12. An apparatus according to claim 1, wherein the at least one light source is held at a substantially fixed angle relative to the reference.

13. An apparatus according to claim 1, wherein the support structure frames the area to be imaged.

14. An apparatus according to claim 1, wherein the light source emits visible light.

15. An apparatus according to claim 1, wherein the reference indicates an environmental condition.

16. An imaging apparatus for obtaining a dental image from a patient comprising:

(a) an intra-oral retainer held in the patient's mouth for illuminating an area of interest, comprising:

(i) a reference coupled to the retainer, disposed within the area of interest;

(ii) at least one light source coupled to the retainer for directing illumination toward the area of interest; and (b) a camera for recording an image from the area of interest using illumination from the light source.

17. An imaging apparatus according to claim 16 wherein the retainer frames the area of interest.

18. An imaging apparatus according to claim 16 wherein the reference is removable.

19. An imaging apparatus according to claim 16 wherein the reference is a color reference.

20. An imaging apparatus according to claim 16 wherein the reference comprises markings for distance measurement.

21. An imaging apparatus according to claim 16 wherein the at least one light source is an LED.

22. An imaging apparatus according to claim 16 wherein the at least one light source is optically coupled with a camera flash apparatus.

23. An imaging apparatus according to claim 16 wherein the at least one light source is electrically coupled with a camera flash control signal.

24. An imaging apparatus according to claim 16 wherein the at least one light source comprises an optical fiber.

25. An imaging apparatus according to claim 16 wherein the camera is a digital camera.

26. An imaging apparatus according to claim 16 wherein the at least one light source is at a fixed angle relative to the area of interest.

27. An imaging apparatus for obtaining a color measurement from a dental structure comprising:

(a) an intra-oral retainer held in a patient's mouth for illuminating the dental structure, comprising:

(i) a color reference coupled to the retainer, disposed proximate the dental structure;

(ii) at least one light source coupled to the retainer for directing illumination toward the dental structure; and (b) a photometric sensing apparatus for recording colorimetric data about the dental structure using illumination from the light source.

28. An imaging apparatus according to claim 27 wherein the sensing apparatus comprises a charge-coupled device.

29. An imaging apparatus according to claim 27 wherein the sensing apparatus is a colorimeter.

30. An imaging apparatus according to claim 27 wherein the sensing apparatus is a spectrophotometer.

31. An intra-oral retainer for illuminating an area of interest within the mouth of a patient, comprising:

(a) a reference coupled to the retainer for placement proximate the area of interest; and (b) at least one light source coupled to the retainer for directing illumination toward the area of interest.

32. An intra-oral retainer according to claim 31 wherein the reference is a color reference.

33. A method for obtaining an image comprising:

(a) coupling at least one light source to a support structure for illuminating an area to be imaged;

(b) coupling a reference element to the support structure, thereby disposing the reference element within the area to be imaged; and (c) coupling the at least one light source to a camera flash mechanism.

34. A method according to claim 33 wherein the step of coupling a reference element comprises the step of coupling a color reference element.

35. A method according to claim 33 wherein the step of coupling at least one light source to a camera flash mechanism comprises the step of transmitting light through an optical fiber 36. A method according to claim 33 further comprising the step of recording the image onto a photosensitive medium.

37. A method according to claim 33 further comprising the step of recording image data in a memory.

38. A method according to claim 33 wherein the support structure frames the area to be imaged.

39. A method for obtaining a photometric characterization of a dental structure from a patient comprising:

(a) mounting a reference element to an intra-oral retainer;

(b) coupling at least one light source to the retainer for directing illumination toward an area of interest comprising the reference element;

(c) fitting the intra-oral retainer in the patient's mouth, defining an imageable area thereby; and (d) obtaining photometric data from within the imageable area using illumination provided from the at least one light source.

40. A method according to claim 39 wherein the step of coupling at least one light source to the retainer comprises the step of connecting an optical fiber.

41. A method according to claim 39 wherein the step of obtaining photometric data comprises the step of obtaining a digital image.

42. A method according to claim 39 further comprising the step of providing the obtained photometric data to a facility for fabrication of a dental structure.

43. A method according to claim 39 wherein the step of coupling at least one light source to the retainer comprises the step of using an optical fiber.

44. A method according to claim 39 wherein the step of mounting a reference element comprises the step of attaching a color reference.

45. A method for obtaining a color value for a dental structure, comprising:
(a) coupling at least one light source to an intra-oral support structure for directing illumination toward an area;
(b) coupling a reference member to the intra-oral support structure within the area illuminated by the at least one light source;
(c) fitting the intra-oral support structure in the patient's mouth, proximate the dental structure, defining an imageable area of the mouth thereby; and
(d) measuring the color value from within the imageable area of the mouth using illumination from the at least one light source.

* * * * *